United States Patent [19]
Kamiya et al.

[11] Patent Number: 5,453,497
[45] Date of Patent: Sep. 26, 1995

[54] PROCESS FOR PRODUCING $N^4$-ACYL-5'-DEOXY-5-FLUOROCYTIDINE COMPOUNDS

[75] Inventors: Takashi Kamiya, Osaka; Makoto Ishiduka; Hiroshi Nakajima, both of Toyama, all of Japan

[73] Assignees: Hoffmann-La Roche Inc., Nutley, N.J.; Fuji Kagaku Kogyo Kabushiki Kaisha, Toyama, Japan

[21] Appl. No.: 168,608

[22] Filed: Dec. 16, 1993

[30] Foreign Application Priority Data

Dec. 18, 1992 [EP] European Pat. Off. ............ 92121539

[51] Int. Cl.$^6$ ...................................................... C07H 1/00
[52] U.S. Cl. .................. 536/28.52; 536/28.5; 536/28.51
[58] Field of Search ................................ 536/28.5, 28.52, 536/28.51

[56] References Cited

U.S. PATENT DOCUMENTS 4,966,891 10/1990 Morio Fujiu et al. ............... 536/28.51

FOREIGN PATENT DOCUMENTS 5076898 1/1978 Japan ..................................... 536/28.5

*Primary Examiner*—Douglas W. Robinson
*Assistant Examiner*—James O. Wilson
*Attorney, Agent, or Firm*—George M. Gould; William H. Epstein; Catherine A. Picut

[57] ABSTRACT

A novel process for producing derivatives of the anti-tumor agent $N^4$-acyl-5'-deoxy-5-fluorocytidine using the novel 5'-deoxy-5-fluoro-$N^4$, 2'-0,3'-0-triacylcytidine derivatives as intermediates is provided.

5-Deoxy-1,2,3-tri-0-acyl-β-D-ribofuranoside is reacted with 5-fluorocytosine to produce 5'-deoxy-2',3'-di-0-acyl-5-fluorocytidine, followed by acylation, to produce the novel intermediate 5'-deoxy-5-flouro-$N^4$,2'-0,3'-0-triacylcytidine. The acyl radicals of this intermediate are selectively de-0-acylated to obtain $N^4$-acyl-5'-deoxy-5-fluorocytidine derivatives. From fluorocytosine, $N^4$-acyl-5'-deoxy-5-fluorocytidine derivatives can be obtained through few steps in high yield, an in satisfactory purity.

1 Claim, No Drawings

PROCESS FOR PRODUCING N⁴-ACYL-5'-DEOXY-5-FLUOROCYTIDINE COMPOUNDS

BACKGROUND OF THE INVENTION $N^4$-acyl-5'-deoxy-5-fluorocytidine derivatives of the formula set forth below are compounds having antitumor activity [Japanese Journal of Cancer Research, Vol. 81, pp. 188–195. (1990)]:

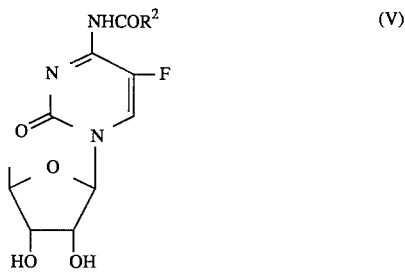

wherein $R^2$ is alkyl, cycloalkyl, alkenyl, aralkyl, aryl or alkoxy.

A process for producing said compounds starting from 5'-deoxy-5-flurocytidine is described in Japanese Patent Application Kokai No. 153,696/1989.

In order to selectively introduce acyl ($R^2CO$) into an amino radical of this compound, a protective radical such as an isopropylidene radical, a silyl radical or the like is first introduced into a hydroxy radical in the sugar part of this compound, subsequently acylating an amino radical in the cytosine-base part and finally eliminating the protective radical using an acid catalyst or the like.

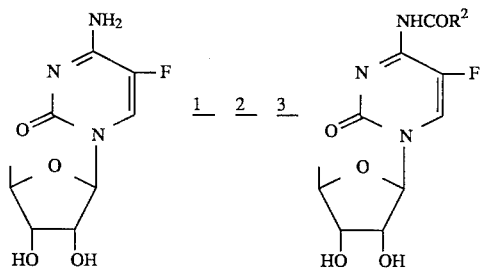

wherein $R^2$ is as above.

That is, the above production method comprises (1) introduction of a protective radical into a hydroxy radical of 5'-deoxy-5-fluorocyctidine, (2) acylation of an amino radical and (3) elimination of said protective radical. In said steps, a protective radical which is an unnecessary radical In the molecular structure of the final compound, must be introduced and eliminated.

In addition, 5'-deoxy-5-fluorocytidine as a starting substance is produced, for example, from 5-fluorocytosine through 5-fluorocytidine [Chem. Pharm. Bull., Vol. 26, No. 10, p. 2,990 (1978)]. However, this method requires many steps (cf., Japanese Patent Publication No. 34,479/1983).

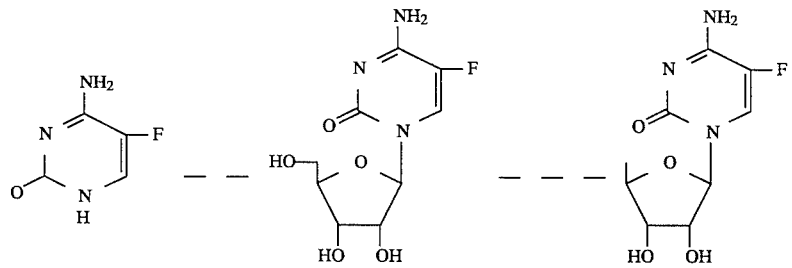

Anyway, the conventional production methods of $N^4$-acyl-5'-deoxy-5-flurocytidine derivatives involve steps in which protection of an hydroxy radical in the sugar part and/or an amino radical in the cytosine part with a suitable protective radical(s) and elimination of said protective radical(s) after completion of the desired reactions. These steps must be carried out repeatedly so that it is difficult to say they are easily performable methods on an industrial scale.

A process for deacylation of $N^4$,0-acylcytidine derivatives has been described [J. H. vanBoom et al, Nucleic Acids Research, Vol. 4 (4), pp. 1,047–1,063 (1977)]. Generally, it is known that 0-acyl is eliminated mainly when $N^4$,0-acylcytidine derivatives react with an alkali. However, the cutting of N-acyl also takes place, so that complicated operations of separation and purification are required in order to obtain a compound from which 0-acyl alone has been eliminated at satisfactory purity.

An $N^4$-acyl radical of $N^4$,0-acylcytidine derivative is relatively easily cut. In case, for example, of $N^4$,2'-0,3'-0, 5'-0-tetracylcytidine derivative, it is known that N-acyl alone can be eliminated selectively only by merely heating the said derivative in alcohol (cf. Japanese Patent Application Kokai No. 23,085/1977).

In addition, it is also known that, when a 5-fluoro-$N^4$, 2'-0,3'-0,5'-0-tetracylcytidine derivative is treated with 0.5N-sodium methoxide in methanol at room temperature, all acyl radicals are eliminated to produce 5-fluorocytidine

[Chem. Pharm. Bull., Vol. 26, No. 10, p. 2,990 (1978)].

SUMMARY OF THE INVENTION

This invention provides a novel process for producing derivatives of the known anti-tumor agent $N^4$-acyl-5'-deoxy-5-fluorocytidine. More particularly, said process is a novel process utilizing, as an intermediate, the novel 5'-deoxy-5-fluoro-$N^4$,2'-0,3'-0-triacylcytidine derivatives of the formula (IV),

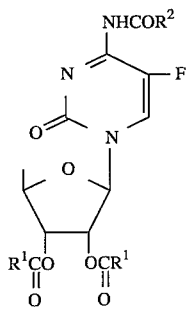

wherein $R^1$ is lower alkyl or aryl which may be substituted or unsubstituted and $R^2$ is alkyl, cycloalkyl, alkenyl, aryl, aralkyl or alkoxy,
and selectively eliminating only an acyl radical from its sugar part. Because of the step of selective deacylation, $N^4$-acyl-5'-deoxy-5-fluorocytidine derivatives can be produced by a process adopting very few steps and in excellent yields, as compared with the conventional processes.

The above step of carrying out selective deacylation has such an exceptional characteristic advantage over the conventional techniques in operation and yield and in the purity of the product.

DETAILED DESCRIPTION OF THE INVENTION

The process for producing $N^4$-acyl-5'-deoxy-5-fluorocytidine (V) is provided firstly:

A process for producing $N^4$-acyl-5'-deoxy-5-fluorocytidine derivatives of the formula (V),

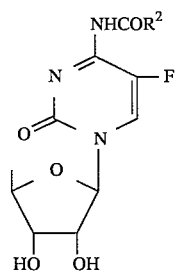

wherein $R^2$ is alkyl, cycloalkyl, alkenyl, aralkyl, aryl or alkoxy, characterized by reacting 5-fluorocytosine with a compound of the formula (II),

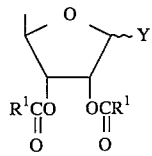

wherein $R^1$ is lower alkyl or aryl which may be substituted or unsubstituted and Y is a halogen, acyloxy or alkoxy, to produce a compound of the formula (III),

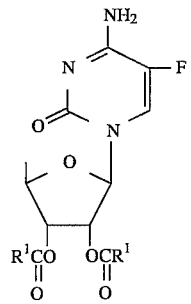

wherein $R^1$ is as above,
acylating the amino radical of this compound to produce a compound of the formula (IV),

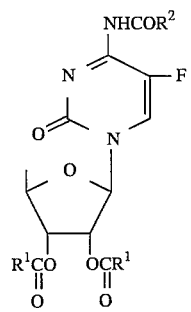

wherein $R^1$ and $R^2$ are as above,
and selectively deacylating only the $R^2CO$ radicals of this compound.

In addition, the present invention provides for a second production process:

A process for producing $N^4$-acyl-5'-deoxy-5-fluorocytidine derivatives of the formula (V),

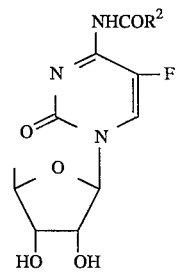

wherein $R^2$ is alkyl, cycloalkyl, alkenyl, aralkyl, aryl or alkoxy, characterized by acylating the amino radical of 5-fluorocytosine to introduce an $R^2CO$ radical therein to produce a compound of the formula (VI),

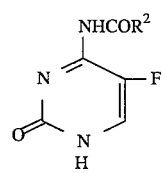

wherein $R^2$ is as above,
reacting this compound with a compound of the formula II,

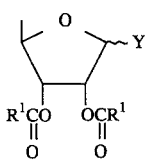

(II)

wherein $R^1$ is lower alkyl or aryl which may be substituted or unsubstituted and Y is a halogen, acyloxy or alkoxy, to produce a compound of the formula (IV),

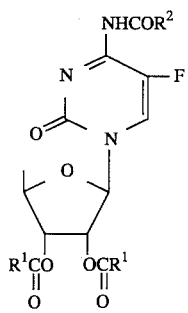

(IV)

wherein $R^1$ and $R^2$ are as above,
and selectively deacylating only the $R^1CO$ radical of this compound.

The above first process is represented by the following reaction formula:

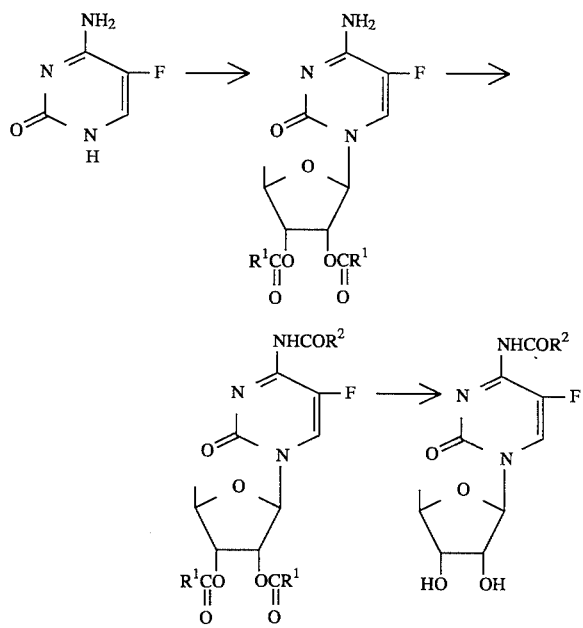

According to the first process of the present invention, $N^4$-acyl- 5'-deoxy-5-fluorocytidine derivatives can be produced using easily available 5-fluorocytosine as a starting material through very few steps, by simple operations, in excellent yields and at satisfactory purities.

Next, the reaction conditions for the above production processes will be described.

The compound of the formula (III) can be obtained by reacting a silylation derivative of 5-fluorocytosine with a compound of the formula (II) in a solvent in the presence of a catalyst generally at a suitable temperature of 0°~100° C.

The silylation derivative of 5-fluorocytosine can be obtained by reacting a silylating agent with 5-fluorocytosine according to a conventional method.

As the above silylating agent, hexamethyldisilazane, trimethylchlorosilane or the like can be enumerated. The amount of a silylating agent to be used is preferably 0.5~2 moles per mole of 5-fluorocytosine.

The reaction time for the above silylation, though it depends upon conditions such as kind of starting materials, reaction temperature, kind of base substances, kind of solvents, etc., is usually several hours.

As solvents to be used for the above condensation reaction, for example, benzene, toluene, xylene, chloroform, methylene chloride, dichloroethane, carbon tetrachloride, 1,2-dichloropropane, 1,1,2,2-tetrachloroethane, acetonitrile, dioxane, tetrahydrofuran, etc., can be enumerated.

In the compound of the formula (II), $R^1$ can be lower alkyl or an aryl which can be substituted or unsubstituted. When $R^1$ is alkyl, lower alkyl containing 1 to 6 carbon atoms is preferred, such as methyl, ethyl, propyl, isopropyl, butyl, isobutyl, or the like. When $R^1$ is unsubstituted aryl, phenyl is enumerated. When $R^1$ is substituted aryl, the preferred groups are methylphenyl, nitrophenyl, halogenophenyl or the like.

Y is a halogen, acyloxy, or alkoxy. When Y is a halogen, Y can be any halogen such as fluorine, chlorine, bromine or iodine. When Y is acyloxy, Y is preferably alkanoyloxy having 2–6 carbon atoms or substituted or unsubstituted benzoyloxy. When Y is substituted benzoyloxy, the preferably substitution groups are lower alkyl containing 1 to 6 carbon atoms, lower alkoxy containing 1 to 6 carbon atoms, nitro or halo. When the substitution group of benzoyloxy is lower alkyl, Y is preferably methylbenzoyloxy. When the substitution group is lower alkoxy, Y is preferably methoxybenzoyloxy. When Y is alkoxy, Y is preferably a lower alkoxy group containing 1 to 7 carbon atoms, such as methoxy, ethoxy or the like.

Compound (II) is obtained from methyl(5-deoxy-2,3-0-isopropylidene)-D-ribofuranoside derivatives which can be obtained from D-ribose (see Japanese Patent Publication No. 40,239/1986). As examples of such derivatives, 5-deoxy-1,2,3-tri-0-acyl-D-ribofuranoside, D-deoxy-2,3-di-0-acyl-1-0-methyl-D-ribofuranoside, 5-deoxy-2,3-di-0-acyl-1-halogen-D-ribofuranoside, etc., can be enumerated.

As examples of the catalyst, Lewis's acids such as tin tetrachloride, zinc chloride, boron fluoride, boron fluoride etherate, aluminum chloride, titanium tetrachloride, antimony chloride, ferric chloride, tin tetrabromide, zinc bromide, zirconium tetrachloride, silver nitrate, etc.; trifluoromethanesulfonic acid; trimethylsilyl trifluoromethanesulfonate; p-toluenesulfonic acid; 2,4-dinitrophenol; etc. are enumerated.

The compound of the formula (III) can also be obtained by reacting the compound of the formula (II) using the aforementioned solvents, catalysts, etc., at a suitable temperature of 0°–100° C., without silylating 5-fluorocytosine.

Alternatively, the compound of the formula (III) can be obtained by heating to melt silylated 5-fluorocytosine or 5-fluorocytosine with the compound of the formula (II) in the presence of a catalyst, e.g., p-toluenesulfonic acid, 2,4-dinitrophenol or the like, without using a solvent.

The compound of formula (IV) can be produced by acylation of the compound of the formula (III) obtained according to the above processes. Said acylation is carried out usually by reacting said compound (III) with an activated carboxylic acid derivative of the formula (VII), $R^2CO—Z$ (VII)

wherein $R^2$ is as above and Z is a leaving radical,
in a solvent in the presence of a base at a suitable temperature.

As examples of the above activated carboxylic acid derivative, acid halide, active ester, acid ester, acid anhydride, mixed acid anhydride, etc., are enumerated. Said activated carboxylic acid derivative can be produced according to a conventional method.

The amount of the compound of the formula (VII) is suitably at least 1 mole per mole of the compound of the formula (III).

The compound of the formula (IV) can be also produced by reacting a compound of the formula (III) and a carboxylic acid represented by the formula, $$R^2\text{—COOH}$$

wherein $R^2$ is as above,
with the addition of a condensing agent, e.g., diethyl cyanophosphate, dicyclohexylcarbodiimide, p-toluenesulfonyl chloride, methanesulfonyl chloride or the like, if necessary, in the presence of a base according to a conventional method.

The mount of the condensing agent is suitably at least 1 mole per mole each of the above carboxylic acids.

The reaction time, though depending upon conditions such as kind of starting materials, reaction temperature, kind of bases, kind of solvents, etc., is usually several minutes to about 20 hours.

The base to be used for the above reaction may be either organic or inorganic. As examples of organic bases, triethylamine, tributylamine, pyridine, N,N-dimethylaminopyridine, lutidine, N-methyl-morphine, etc. are enumerated. When the base is inorganic, hydroxides, carbonates or alkoxides of alkali metals or alkaline earth metals, e.g., sodium hydroxide, sodium carbonate, sodium bicarbonate, sodium methoxide or their lithium salt, potassium salt, calcium salt, barium salt, etc. can be enumerated.

Where $R^2$ is an alkyl group, it includes straight chain and branched chain alkyl groups having 1–22 carbon atoms, for example, methyl, ethyl, propyl, isopropyl, butyl, isobutyl, sec-butyl, tert-butyl, pentyl, isopentyl, neopentyl, hexyl, isohexyl, heptyl, octyl, nonyl, decyl, undecyl, dodecyl, tridecyl, tetradecyl, pentadecyl, hexadecyl, heptadecyl, nonadecyl, etc.

When $R^2$ is cycloalkyl, it includes any cycloalkyl containing 3–12 carbon atoms, such as cyclopropyl, cyclobutyl, cyclopentyl, cyclohexyl, adamantyl, or the like.

When $R^2$ is alkenyl, it includes both substituted and unsubstituted alkenyl radicals having 2–22 carbon atoms. When alkenyl is unsubstituted, allyl, 1-propenyl, butenyl, hexenyl, decenyl, undecenyl, tridecenyl, pentadecenyl, heptadecenyl, heptadecadienyl, pentatridecatrienyl, nonadecenyl, nonadecadienyl, nonadecatetraenyl, etc. are enumerated.

When $R^2$ is substituted alkenyl, the preferably substitution groups are lower alkyl or aryl. When the substitution group is lower alkyl, $R^2$ is preferably 3-methyl-2-butenyl, or 1-methyl-2-propenyl. When the substitution group is aryl, 2-phenylvinyl is preferred.

The aryl designates both substitued and unsubstituted aryl. The term aryl signifies mononuclear aromatic hydrocarbon groups such as phenyl, and polynuclear aryl groups such as naphthyl, anthryl, phenanthryl, etc. The mononuclear and polynuclear aryl groups can be substituted in one or more positions. When $R^2$ is mononuclear unsubstituted aryl, phenyl is the preferred radical. When $R^2$ is mononuclear substituted aryl, the preferred substitutions are lower alkyl containing 1 to 6 carbon atoms, halo, lower alkoxy having 1 to 7 carbon atoms, lower alklenedioxy, lower alkylthio, nitro, cyano, acetyl, carbamoyl, and lower alkoxycarbamoyl. When the substitution is lower alkyl, then $R^2$ is preferably tolyl, xylyl, mesityl, cumenyl and ethylphenyl. When the substitution is halo, $R^2$ is preferably fluorophenyl, chlorophenyl, bromophenyl, iodophenyl, difluorophenyl and dichlorophenyl. When the substitution is lower alkoxy, then methoxyphenyl, dimethoxyphenyl, trimethoxyphenyl, ethoxyphenyl, diethoxyphenyl, triethoxyphenyl, propoxyphenyl. etc., are enumerated. When the substitution is lower alkalenedioxy, methylenedioxyphenyl is the preferred $R^2$ group. When the substitution is lower alkylthio, then $R^2$ is preferably (methylthio) phenyl. When the substitution is lower alkoxycarbamoyl, then $R^2$ is preferably methoxycarbamoylphenyl.

The mononuclear and polynuclear aryl radicals may contain heteroatoms, wherein the heteroatoms are selected from the group consisting of nitrogen, oxygen, or sulfur. These heteroaryls can be unsubstituted or substituted with the above mentioned substitutions.

When $R^2$ is a mononuclear heteroaryl, then $R^2$ may be thienyl, methylthienyl, furyl, nitrofuryl, etc.

The preferred polynuclear aryl groups include napthyl, biphenylyl, pyrrolyl, methylpyrrolyl, imidazolyl, pyrazolyl, pyridyl, methylpyridyl, pyrazinyl, or the like.

When $R^2$ is aralkyl, aralkyl denotes aryl lower alkyl groups, wherein aryl is defined as above and lower alkyl contains 1 to 6 carbon atoms. The aryl group can be unsubstituted or substituted with the substitutents described with respect to aryl above. The preferred unsubstituted aralkyl groups include benzyl and 1-phenylethyl. The substituted aralkyls include methylbenzyl, fluorobenzyl, chlorobenzyl, methoxybenzyl, dimethoxybenzyl, nitrobenzyl, phenethyl, picolyl, 3-indolylmethyl or the like.

As used throughout this specification, alkoxy designates an alkoxy group containing 1 to 9 carbon atoms. When $R^2$ is alkoxy, the preferred groups are methoxy, ethoxy, propoxy, butoxy, pentyloxy, hexyloxy, octyloxy, nonyloxy, etc.

The solvents to be used for the above acylation may be polar or non-polar. The preferred polar solvents include acetonitrile, nitromethane, dimethyl formamide, acetone, dimethyl acetoamide, hexamethyl phosphoamide, dimethyl sulfoxide, pyridine, lutidine, and the like. The preferred non-polar solvents include chloroform, di-chloroethane, methylenechloride, toluene, etc.

In the above production process, the reaction proceeds very readily, and the compound of the formula (IV) is obtained at a satisfactory purity and in good yields usually be treating the reaction solution according to a conventional method and then addition an appropriate solvent to the residue to recrystallize the same readily. In addition, the compound is obtained at good purity and in good yields, so that it can be used for the reaction in the next step as it is without particularly conducting isolation. By recrystallizing, more highly purified compound can be readily obtained.

As solvents to be used for said recrystallizing, for example, alcohols such as methanol, ethanol, isopropyl alcohol, etc.; ethers such as isopropyl ether, etc.; methyl acetate; ethylacetate; or the like can be enumerated.

Next, the reaction for producing $N^4$-acyl-5'-deoxy-5-fluorocytidine derivatives from the compound of the formula (IV) obtained according to the above process will be described.

The present inventors found that only acyl of an 0-acyl radical was selectively eliminated from the compound of the formula (IV) in a solvent in the presence of a base to give $N^4$-acyl-5'-deoxy-5-fluorocytidine derivatives of the formula (V).

This reaction is represented by the following reaction formula:

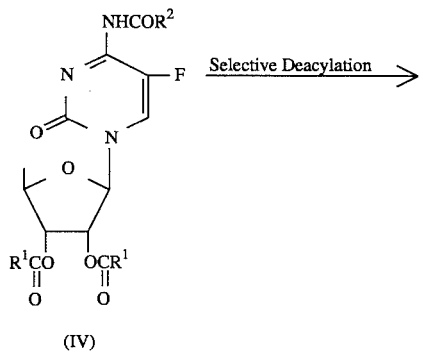

(IV)

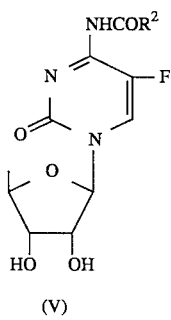

(V)

wherein $R^1$ and $R^2$ are as above.

In accordance with this reaction, selective deacylation occurs by treating a compund of the formula (IV) with a solvent in the presence of a base.

The temperature in this step of deacylation is not a critical feature and best results may vary depending upon kind of materials, kind of solvents, kind of bases, concentration of the respective bases, etc. Usually, the reaction temperature is at or below room temperature, preferably between 0° and 30° C.

The reaction time for the above mentioned step is also not a critical feature, and best results may vary depending upon kind of starting materials, reaction temperature, kind of bases, kind of solvent, etc. Usually, the reaction time is within the range of several minutes to about 20 hours.

In carrying out this reaction of selective deacylation, the bases used for the reaction are dissolved in water or an organic solvent or a mixed solution of water and an organic solvent. Conventional inorganic or organic bases may be used. Among the preferred inorganic bases selected are those from the group consisting of hydroxides, carbonates or alkoxide of alkali metal or alkaline earth metals, such as sodium hydroxide, sodium carbonate, sodium bicarbonate, sodium methoxide, or their lithium salt, potassium salt, calcium salt, barium salt, etc. Among the preferred organic bases are those selected from the group consisting of ammonia, triethylamine, DBU, tetramethylammonium hydroxide, strongly basic anion exchange resins (OH-type), etc.

These bases can be used at a suitable concentration. However, it is usually preferred to use the same as a solution of 0.4–2N.

In addition, the mount of base, though depending upon kind and combination of solvents to be used, is suitably 1 mole equivalent of the compound of the formula (IV), preferably with the range of 1 to 4 mole equivalents. It is advantageous industrially to use inorganic bases which are inexpensive.

In carrying out the above reaction, any conventional inert polar or non-polar solvent can be used. The preferred polar solvents are water and alcohols selected from group consisting of methanol, ethanol, propanol, butanol, isopropanol, ethers such as tetrahydrofuran, dioxane; acetones; and acid amides such as dimethyl formamide. Among the non-polar solvents are carbon halogenides such as methylene chloride, chloroform, etc.; aromatic hydrocarbons such as toluene, xylene, etc. These solvents can be used independently or in combination.

In case or using a heterogeneous system, e.g., water and methylene chloride, etc., the aimed product can be obtained in satisfactory yields.

In addition, when solvents are of such a heterogeneous system, the reaction may be carried out by adding a phase-transfer catalyst.

After the completion of reaction, the compound of the formula (V) is obtained using a combination of conventional separation and purification methods.

As described above, the selective deacylation step has an industrially very significant advantage because the compound of the formula (V) can be produced from the compound of the formula (IV) by using an inexpensive base, by simple procedures, at good purity and at satisfactory yields.

The yields in each step of the above production processes are very high, so it is possible to transfer to the next step without isolating and purifying an intermediate.

The aforementioned novel compound IV can also be produced from 5-flurorocytosine by acylating 5-fluorocytosine and then reacting the obtained compound of formula (VI),

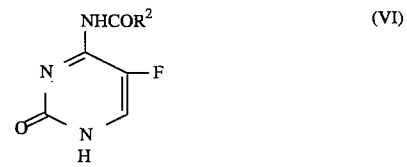

wherein $R^2$ is as above, i.e., $N^4$-acyl-5-fluorocytosine derivative, with the compound of formula (II).

Therefore, the second process as described above is provided by the present invention.

Acylation of 5-fluorocytosine is carried out by reacting 5-fluorocytosine with the aforementioned above compound of formula (VII) in a solvent at a suitable temperature between room temperature and reflux temperature according to a conventional method. The temperature is not a critical aspect of this reaction.

The reaction time, though depending upon conditions such as kind of starting materials, reaction temperature, kind of bases, kind of solvents, etc., is usually several minutes to several hours.

As solvents, those used in the acylation in the aforementioned first process are used.

The mount of acylating agent is suitably at least 1 mole per mole of 5-fluorocytosine.

According to this second production process, the compound of the formula (IV) is obtained by silylating the compound of the formula (VI) obtained according to the above production process by using the aforementioned silylating agent and then reacting the resulting compound with compound of formula (II) in a solvent or in the absence of a solvent in the presence of a catalyst.

The reaction of the compound of formula (VI) or a silylation derivative of the compound of formula (VI) with the compound of formula (II) can be carried out under the same conditions as the aforementioned conditions for reacting 5-fluorocytosine with the compound of formula (II).

The amount of the silylating agent to be used is preferably 0.5–2 moles per mole of the compound of the formula (VI).

The reaction temperature is not critical, and is usually carried out at or below room temperature. If necessary, ice-cooling may be adopted.

The reaction time, though depending upon conditions such as kind of starting materials, reaction temperature, kind of solvents, etc., is usually several hours.

The production process of a compound of formula (IV) is represented by the following reaction formula:

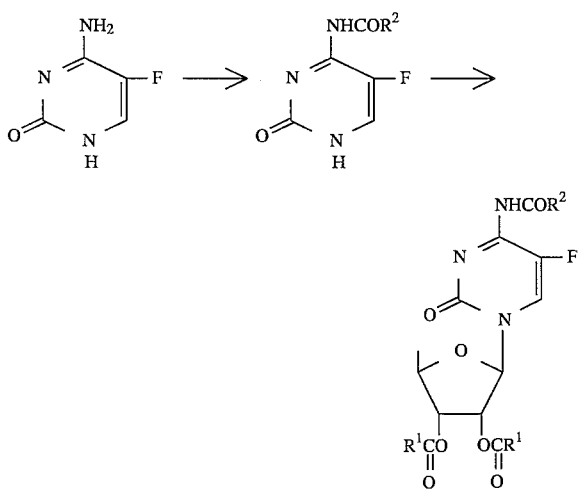

wherein $R^1$ and $R^2$ are as above.

The compound of the formula (IV) can be obtained also by reacting the compound of formula (VI) with the compound of formula (II) with or without a solvent in the presence of a catalyst in the same manner as aforementioned.

The compounds of formula (IV) are novel compounds.

Hereinafter, typical compounds of formula (IV) will be exemplified.

5'-deoxy-2',3'-di-0-acetyl-5-fluoro-$N^4$-palmitoylcytidine,
5'-deoxy-2',3'-di-0-acetyl-5-fluoro-$N^4$-octyloxycarbonylcytidine,
5'-deoxy-2',3'-di-0-acetyl-5-fluoro-$N^4$-(3-methylbenzoyl)cytidine,
5'-deoxy-2',3'-di-0-acetyl-5-fluoro-$N^4$-(3,4,5-trimethoxybenzoyl)cytidine,
5'-deoxy-2',3'-di-0-acetyl-5-fluoro-$N^4$-(2-methoxybenzoyl)cytidine.
$N^4$-(4-chlorobenzoyl)-5'-deoxy-2',3'-di-0-acetyl-5-fluorocytidine,
5'-deoxy-2',3'-di-0-acetyl-5-fluoro-$N^4$-(4-nitrobenzoyl)cytidine,
5'-deoxy-2',3'-di-0-acetyl-5-fluoro-$N^4$-(2-furoyl)cytidine,
5'-deoxy-2',3'-di-0-acetyl-5-fluoro-$N^4$-(nicotinoyl)cytidine,
5'-deoxy-2',3'-di-0-acetyl-5-fluoro-$N^4$-(2-thenoyl)cytidine,
$N^4$-crotonoyl-5'-deoxy-2',3'-di-0-acetyl-5-fluorocytidine,
$N^4$-cyclohexanecarbonyl- 5-deoxy-2',3'-di-0-acetyl-5-fluorocytidine,
5'-deoxy-2',3'-di-0-acetyl-5-fluoro-$N^4$-(phenylacetyl)cytidine, and
5'-deoxy-2',3'-di-0-toluoyl-5-fluoro-$N^4$-(3,4,5-trimethoxybenzoyl)cytidine.

Hereinafter, the present process will be described specifically, referring to examples.

EXAMPLES

Example 1

25.8 g of 5-fluorocytosine was suspended in 103 ml of toluene and 32.3 g of hexamethyldisilazane. The mixture was heated to react at 110° C. for 3 hours. After concentrating the reaction solution under reduced pressure, 330 ml of methylene chloride and 59.3 g of 5-deoxy-1,2,3-tri-0-acetyl-β-D-ribofuranoside were added to the residue. Then, 62.5 g of anhydrous stannic chloride was added dropwise thereto over a period of 10 minutes while ice-cooling. After stirring the mixture at room temperature for additional 2 hours, 101 g of sodium bicarbonate was added, and followed by dropwise addition of 35 ml of water thereto over a period of 20 minutes. After stirring the resulting mixture at room temperature for 3 hours, insoluble material was filtered out and the filtrate was washed with 100 ml of 4% sodium bicarbonate solution. After removal of the solvent under reduced pressure, the residue was recrystallized by adding 180 ml of isopropanol thereto. Then, crystals were collected to obtain 49.9 g (76%) of 5-deoxy-2',3'-di-0-acetyl-5-fluorocytidine.

The melting point of a product after recrystallization of the above crystals from isopropanol was 191.5°–193.2° C. UV Absorption Spectrum: λ max ($H_2O$) nm: 278 (ε=7,800), 239 (ε=8,800), 193 (ε=19,100) Optical Rotation: [α]D(20° C.):+86 ($CHCl_3$, C=1) $^1$H-NMR (90 MHz, $CDCl_3$): 1.45 (d, J=6.4 Hz, 3H), 2.08 (s, 3H), 2.09 (s, 3H), 5.96 (dd, (J=4.4 Hz, 1.5 Hz), 1H), 7.38 (d, J=6.4 Hz, 1H)

Example 2

1.29 of 5-fluorocytosine was suspended in a solution of 16.5 ml of methylene chloride and 3.4 ml of acetonitrile. After adding 2.97 g of 5-deoxy-1,2,3-tri-0-acetyl-β-D-ribofuranoside to the suspension, 3.91 g of anhydrous stannic chloride was dropwise added thereto in 5 minutes at room temperature. This solution was stirred at room temperature for 3 more hours, followed by subjecting the same after treatment as in Example 1. After recrystallizing the residue by adding 7.4 ml of ethanol thereto, crystals were filtered off to give 2.12 g (64.4%) of 5'-deoxy-2',3'-di-0-acetyl-5-fluorocytidine.

The results of instrumental analysis of the obtained compound were identical with those of Example 1.

Example 3

0.52 g pf 5-fluorocytosine was suspended in a solution of 2 ml of toluene and 0.42 g of hexamethyldisilazane, and the mixture was heated at 110° C. for 3 hours. After concentrating the reaction mixture under reduced pressure, 6.6 ml of methylene chloride and 1.19 g of 5'-deoxy-1,2,3-tri-0-acetyl-β-D-ribofuranoside were added to the residue. Then, 1.07 g of trimethylsilyl trifluoromethanesulfonate was added thereto at room temperature. After stirring the mixture at room temperature for overnight, 13 ml of saturated sodium bicarbonate was added thereto. The mixture was stirred at room temperature for 30 minutes. After separation of the organic layer, the aqueous layer was extracted with 5 ml of methylene chloride. The organic layers were combined, and washed with water. After removal of the solvent under reduced pressure, the residue was recrystallized from 6 ml of isopropanol to give 0.69 g (52.4%) of 5'-deoxy-2',3'-di-0-acetyl-5-fluorocytidine.

The results of instrumental analysis of the obtained compound were identical with those of Example 1.

Example 4

38 g of 5'-deoxy-2',3'-di-0-acetyl-5-fluorocytidine obtained according to the method of Example 1 was dissolved in 190 ml of methylene chloride, followed by addition of 14.3 g of pyridine. To this solution, was added 34.6 g of 3,4,5-trimethoxybenzoyl chloride at room temperature. After stirring at room temperature for overnight, the resulting solution was extracted with 152 ml of methylene chloride and 76 ml of water. The organic layer was separated and washed with 76 ml of 4% sodium bicarbonate solution, and the solvent was distilled under reduced pressure. The residue was recrystallized by adding 620 ml of methanol thereto to obtain 58.2 g (96.4%) of 5'-deoxy-2',3'-di-0-acetyl-5-fluoro-$N^4$-(3,4,5-trimethoxybenzoyl)cytidine as crystalline powder. The melting point of a product obtained by recrystallizing these crystals from ethylacetate was 130.8°–133.2° C., UV Absorption Spectrum: λ max ($H_2O$) nm: 314 ($\epsilon$=16,300), 255 ($\epsilon$=11,100), 209 ($\epsilon$=36,800) Optical Rotation: [α]D(20° C.):+45 (CHCl$_3$, C=1) $^1$H-NMR (90 MHz, CDCl$_{l3}$): 1.48 (d J=6.4 Hz 3H) 2.10 (s, 3H), 2.12 (s, 3H), 3.92 (s, 3H) 3.93 (s, 6H) 5.98 (dd (J=4.9 Hz, 1.0 Hz), 1H), 7.48 (d, (J=5.4 Hz, 1H), 7.5 ( s, 2H)

Examples 5–16

In the same manner as in Example 4, compounds given in Tables 1, 2 and 3 were synthesized.

TABLE 1

Compounds Obtained

| | In Formula (IV) | | mp | $^1$H-NMR (90 |
| | $R^1$ | $R^2$ | (°C.) | MHz) δ ppm |
|---|---|---|---|---|
| Example 5 | Me | CH$_3$—(CH$_2$)$_{14}$— | 78.6–79.7 | (CDCl$_3$): 0.88 (bt, 3H), 1.25 (s, methylene), 1.47 (d, 3H), 2.10 (s, 3H), 2.11 (s, 3H), 4.28 (m, 1H), 4.99 (t, 1H), 5.35 (t, 1H), 5.95 (dd, 1H), 7.59 (d, 1H) |
| Example 6 | Me | CH$_3$—(CH$_2$)$_7$O— | Oily Substance | (CDCl$_3$): 0.88 (bt, 3H), 1.29 (bs, 10H), 1.47 (d, 3H), 1.71 (m, 2H), 2.10 (s, 3H), 2.11 (s, 3H), 4.17 (t, 2H), 5.01 (t, 1H), 5.29 (t, 1H), 5.96 (dd, 1H), 7.43 (d, 1H) |
| Example 7 | Me | 4-Chlorophenyl- | 128.4–129.7 | (CDCl$_3$): 1.49 (d, 3H), 2.10 (s, 3H), 2.13 (s, 3H), 4.26 (m, 1H), 5.03 (t, 1H), 5.31 (t, 1H), 5.98 (dd, 1H), 7.42 (d, 2H), 7.50 (d, 1H), 8.24 (d, 2H) |
| Example 8 | Me | 2-Methoxyphenyl- | 139.3–147.0 | (CDCl$_3$): 1.49 (d, 3H), 2.10 (s, 3H), 2.11 (s, 3H), 4.06 (s, 3H), 4.30 (m, 1H), 5.01 (t, 1H), 5.34 (t, 1H), 6.11 (dd, 1H), 7.69 (d, 1H), 8.25 (dd, 1H) |
| Example 9 | Me | 3-Methylphenyl- | 169.2–170.4 | (CDCl$_3$): 1.48 (d, 3H), 2.10 (s, 3H), 2.11 (s, 3H), 2.41 (s, 3H), 4.25 (m, 1H), 5.03 (t, 1H), 5.33 (t, 1H), 5.98 (dd, 1H), 7.31–7.38 (m, 2H), 7.52 (d, 1H), 8.07 (m, 2H) |

TABLE 2

Compounds Obtained

| | In Formula (IV) | | mp | $^1$H-NMR (90 MHz) |
| | $R^1$ | $R^2$ | (°C.) | δ ppm |
|---|---|---|---|---|
| Example 10 | Me | 4-Nitrophenyl- | 186.8–187.9 | (CDCl$_3$): 1.50 (d, 3H), 2.11 (s, 3H), 2.13 (s, 3H), 4.28 (m, 1H), 5.04 (t, 1H), 5.33 (t, 1H), 5.98 (dd, 1H), 7.57 (d, 1H), 8.21–8.52 (m, 4H) |
| Example 11 | Me | 3-Pyridyl- | Amorphous powder | (CDCl$_3$): 1.49 (d, 3H), 2.11 (s, 3H), 2.13 (s, 3H), 4.28 (m, 1H), 5.04 (t, 1H), 5.33 (t, 1H), 5.98 (dd, 1H), 7.40 (m, 1H), 7.55 (d, 1H), 8.52 (m, 1H), 8.76 (dd, 1H), 9.47 (dd, 1H) |
| Example 12 | Me | 2-Furyl- | 139.6–140.8 | (CDCl$_3$): 1.48 (d, 3H), 2.10 (s, 3H), 2.12 (s, 3H), 4.26 (m, 1H), 5.03 (t, 1H), 5.32 (t, 1H), 5.98 (dd, 1H), 6.55 (dd, 1H), 7.41 (dd, 1H), 7.52 (d, 1H), 7.64 (dd, 1H) |
| Example 13 | Me | 2-Thienyl- | 154.0–154.8 | (CDCl$_3$): 1.48 (d, 3H), 2.10 (s, 3H), 2.12 (s, 3H), 4.25 (m, 1H), 5.03 (t, 1H), 5.31 (t, 1H), 5.97 (dd, 1H), 7.13 (dd, 1H), 7.48 (d, 1H), 7.61 (dd, 1H), 7.96 (dd, 1H) |
| Example 14 | Me | 1-Propenyl- | 95.0–97.0 | (CDCl$_3$): 1.47 (d, 3H), 1.95 (dd, 3H), 2.11 (s, 6H), 4.27 (m, 1H), 5.01 (t, 1H), 5.33 (t, 1H), 5.96 (dd, 1H), 7.04–7.45 (m, 1H), 7.55 (d, 1H) |

TABLE 3

| | Compounds Obtained | | |
|---|---|---|---|
| | In Formula (IV) | mp | $^1$H-NMR (90 MHz) |
| | $R^1$ | $R^2$ | (°C.) | δ ppm |
| Example 15 | Me | Cyclohexyl— | 154.2~155.1 | (CDCl$_3$): 1.47 (d, 3H), 1.1~2.2 (m, 10H), 2.10 (s, 3H), 2.11 (s, 3H), 4.28 (m, 1H), 4.99 (t, 1H), 5.35 (t, 1H), 5.94 (dd, 1H), 7.60 (d, 1H) |
| Example 16 | Me | Benzyl— | 118.5~119.8 | (CDCl$_3$): 1.46 (d, 3H), 2.09 (s, 3H), 2.10 (s, 3H), 4.21 (s, 2H), 4.28 (m, 1H), 4.99 (t, 1H), 5.35 (t, 1H), 5.95 (dd, 1H), 7.30 (s, 5H), 7.63 (d, 1H) |

Example 17

1.10 g of 3,4,5-trimethoxybenzoic acid was dissolved in 12 ml of methylene chloride and 1.65 g of pyridine, followed by addition of 0.60 g of methanesulfonyl chloride at room temperature. After the mixture was stirred at room temperature for 2 hours, 1.32 g of 5'-deoxy-2',3'-di-0-acetyl-5-fluorocytidine was added to the solution. After stirring at room temperature for 66 hours, the resulting solution was extracted by adding 10 ml of water thereto. The organic layer was separated and washed with 10 ml of 4% sodium bicarbonate solution. After removal of the solvent under reduced pressure, the residue was recrystallized from ethyl acetate to obtain 1.27 g (60.5%) of 5'-deoxy-2',3'-di-0-acetyl-5-fluoro-N$^4$-(3,4,5-trimethoxybenzoyl)cytidine as crystalline powder.

The results of instrumental analysis were identical with those obtained in Example 4.

Example 18

12.9 g of 5-fluorocytosine was suspended in 78 ml of pyridine, followed by addition of 23.1 g of 3,4,5-trimethoxybenzoyl chloride and stirring at 100° C. for 5 hours. The reaction mixture was cooled down to room temperature and then poured into 310 ml of water at room temperature over a period of 20 minutes. The precipitated crystals were collected by filtration to obtain 29.2 g (90.4%) of 5-fluoro-N$^4$-(3,4,5-trimethoxybenzoyl)cytosine.

The melting point of a product obtained by recrystalizing 14.6 g of the above product from 600 ml of methanol was 201.4°–202.2° C. (decomposed) $^1$H-NMR (90 MHz, DMSO-d$_6$): 3.74 (s, 3H), 3.84 (s, 6H), 7.37 (s, 2H), 8.09 (d, J=5.9 Hz, 1H) 6.47 g of 5-fluoro-N$^4$-(3,4,5-trimethoxybenzoyl)cytosine obtained by the above method were suspended in 10 ml of toluene and 2.10 g of hexamethyldisilazane to react at 100° C. for 3 hours. The reaction solution was concentrated under reduced pressure. Then, 60 ml of methylene chloroide and 5.93 g of 5-deoxy-1,2,3-tri-0-acetyl-β-D-ribofuranoside were added to the residue, followed by adding dropwise 6.25 g of anhydrous stannic chloride while ice-cooling. This reaction solution was stirred at room temperature for further 30 minutes, followed by addition of 10.1 g of sodium bicarbonate. At room temperature, 3.5 ml of water was then added thereto over a period of 10 minutes. After stirring at room temperature for 3 hours, insoluble matters were filtered out, and the filtrate was washed with 10 ml of 6% sodium bicarbonate solution. After the removal of the solvent under reduced pressure, the residue was recrystallized by addition of 100 ml of methanol to obtain 8.20 g (78.3%) of 5'-deoxy-2',3'-di-0-acetyl-5-fluoro-N$^4$-(3,4,5-trimethoxybenzoyl)cytidine as crystalline powder.

The results of instrument analysis of the obtained compound was identical with those of Example 4.

Example 19

5.55 g of 5-fluoro-N$^4$-(3,4,5-trimethoxybenzoyl)cytidine was suspended in 70 ml of methylene chloride. After adding 5.09 g of 5-deoxy-1,2,3-tri-0-acetyl-β-D-ribofuranoside to the suspension. 5.36 g of anhydrous stannic chloride was dropwise added thereto at room temperature over a period of 5 minutes. This reaction solution was stirred at room temperature for further 45 minutes. Therafter, the reaction mixture was subjected to the same after-treatment as in Example 18 to obtain 6.17 g (68.6%) of 5'-deoxy-2',3'-di-0-acetyl-5-fluoro-N$^4$-(3,4,5-trimethoxybenzoyl)cytidine.

The results of instrumental analysis of the obtained compound were identical with those of Example 4.

Example 20

35.5 g of 5'-deoxy-2',3'-di-0-acetyl-5-fluoro-N$^4$-(3,4,5-trimethoxybenzoyl)cytidine obtained according to the method of Example 4 was dissolved in 300 ml of methylene chloride, to which 270 ml of aqueous 1N-NaOH solution was dropwise added with stirring while ice-cooling. After stirring the solution for 30 minutes at the same temperature. 30 ml of methanol was added to the reaction solution. After dropwise adding conc. hydrochloric acid thereto to adjust the pH to 6, under ice-cooling the organic layer was separated, washed with 60 ml of water and then concentrated under reduced pressure. The residue was crystallized from 150 ml of ethyl acetate and filtered to obtain 25.4 g (85.4%) of 5'-deoxy-5-fluoro-N$^4$-(3,4,5-trimethoxybenzoyl)cytidine as crystals. The melting point of a product obtained by recrystallizing these crystals from ethyl acetate was 167.0°–168.4° C. $^1$H-NMR (90 MHz, DMSO-d$_6$) 1.34 (d, 3H), 3.75 (s, 3H), 3.85 (s, 6H), 5.08 (d, 1H), 5.45 (d, 1H), 5.73 (d, 1H) 7.36 (s, 2H), 8.22 (d, 1H)

Example 21

52.3 mg of 5'-deoxy-2',3'-di-0-acetyl-5-fluoro-N$^4$-(3,4,5-trimethoxybenzoyl)cytidine was added to 0.4 ml of N-NaOH, and the mixture was stirred at 26° C. for 5 minutes. As a result of confirming the state of reaction progress by TLC, the spot for the starting material had disappeared completely and that for 5'-deoxy-5-fluoro-N$^4$-(3,4,5-trimethoxybenzoyl)cytidine alone was found. After the completion of reaction, methylene chloride was added to the reaction solution. Then, the pH of the solution was adjusted to pH 6 by dropwise addition of conc. hydrochloric acid. The organic layer was separated, washed with water and then concentrated under reduced pressure. The residue was recrystallized from ethyl acetate to obtain 5'-deoxy-5-fluoro-N$^4$-(3,4,5-trimethoxybenzoyl )cytidine.

The results of instruental analysis were identical with those of Example 20.

Example 22–31

According to the method of Example 21, the reaction was carried out by so selecting the compound of the formula (IV), kind of solvents, kind and mount of bases, reaction time and reaction temperature as given in Table 4 set forth below. Thereafter, the after-treatment was carried out in the same manner as in Example 21 to obtain 5'-deoxy-5-fluoro-$N^4$-(3,4,5-trimethoxybenzoyl)cytidine.

As a result of confirming the state of reaction progress in each example after each reaction time, the spot for the starting material had disappeared completely and that for 5'-deoxy-5-fluoro-$N^4$-(3,4,5-trimethoxybenzoyl)cytidine alone was found.

of reaction progress, the spot for the starting material had disappeared completely and that for the aimed product alone was found. Therafter, the reaction solution was treated in the same manner as in Example 32, and the obtained residue was recrystallized from ethyl acetate to obtain 0.40 g (49.8%) of $N^4$-(4-chlorobenzoyl)-5'-deoxy-5-fluorocytidine.

The results of instrumental analysis of the obtained compound were given below. Melting point: 142.3°–145.6° C. $^1$H-NMR (90 MHz, DMSO-$d_6$): 1.32 (d, 3H), 3.5–4.2 (m, 3H), 5.08 (d, 1H), 5.42 (d, 1H), 5.71 (dd, 1H), 7.58 (d, 2H), 8.02 (d, 1H), 8.02 (d, 2H)

TABLE 4

| Example No. | Compound Used In Formula (IV) $R_1$ | $R_2$ | Solvent Added (ml) | Kind and Amount of Base Used (mmol) | Time (min.) | Reaction Temperature (°C.) |
|---|---|---|---|---|---|---|
| Example 22 | Me | Tri-MeO—$C_6H_2$— (0.1 mmol) | MeOH (1.1) | N—NaOH (0.4) | 5 | 26 |
| Example 23 | Me | Tri-MeO—$C_6H_2$— (0.1 mmol) | THF (1.4) MeOH (1.1) | N—NaOH (0.6) | 5 | 0 |
| Example 24 | Me | Tri-MeO—$C_6H_2$— (0.1 mmol) | THF (1.4) MeOH (1.1) | 1/6 N—NaOH (0.1) | 60 | 30 |
| Example 25 | Me | Tri-MeO—$C_6H_2$— (0.1 mmol) | THF (1.4) MeOH (1.1) | N—KOH (0.6) | 5 | 30 |
| Example 26 | Me | Tri-MeO—$C_6H_2$— (0.1 mmol) | THF (1.4) MeOH (1.1) | 0.6M Ba(OH)$_2$ (0.6) | 5 | 30 |
| Example 27 | Me | Tri-MeO—$C_6H_2$— (0.1 mmol) | THF (1.4) MeOH (1.1) | 0.6M Ca(OH)$_2$ (0.6) | 5 | 30 |
| Example 28 | Me | Tri-MeO—$C_6H_2$— (0.1 mmol) | THF (1.4) MeOH (1.1) | 1M Na$_2$CO$_3$ (0.6) | 60 | 30 |
| Example 29 | Me | Tri-MeO—$C_6H_2$— (0.1 mmol) | THF (1.4) MeOH (1.1) | Sat. NaHCO$_3$ (0.6) | 240 | 30 |
| Example 30 | Me | Tri-MeO—$C_6H_2$— (1 mmol) | MEOH (20) | MeONa (2.0) | 5 | 30 |
| Example 31 | 4-Me—Phe | Tri-MeO—$C_6H_2$— (2 mmol) | THF (14) MeOH (11) | N—NaOH (8.0) | 5 | 30 |

Example 32

1.14 g of 5'-deoxy-2',3'-di-0-acetyl-5-fluoro-$N^4$-(palmitoyl)cytidine was dissolved in 14 ml of THF and 11 ml of methanol, followed by addition of 8 ml of N-NaOH at 30° C. and 5-minute stirring. As a result of confirming the state of reaction progress by TLC, the spot for the starting material had disappeared completely and that for the aimed product alone was found. Then, 10% hyclrochloric acid was added to the reaction solution to adjust the pH to 5. After removal of the organic solvent under reduced pressure, the residue was extracted with 100 ml of methylene chloride. The organic layer was separated, washed with water and concentrated under reduced pressure. After recrystallizing the residue from 7 ml of methanol, the crystals were filtered to obtain 0.64 g (66%) of 5'-deoxy-5-fluoro-$N^4$-(palmitoyl)cytidine.

The results of instrumental analysis of the obtained compound were as follows. Melting point: 93.0°–95.0° C. $^1$H-NMR (90 MHz, DMSO-$d_6$): 0.86 (t, 3H), 1.24 (s, methylene), 1.33 (d, 3H), 3.5–4.15 (m, 3H), 5.04 (d, 1H), 5.42 (d, 1H), 5.68 (dd, 1H), 8.08 (d, 1H)

Example 33

0.98 g of 5'-deoxy-2',3'-di-0-acetyl-5-fluoro-$N^4$-(4-chlorobenzoyl)cytidine was dissolved in 14 ml of THF and 1 ml of methanol, followed by addition of 8 ml of N-NaOH at 30° C. and 5-minute stirring. As a result of confirming the state

Example 34

To a solution of 0.93 g of 5'-deoxy-2',3'-di-0-acetyl-5-fluoro-$N^4$-(2-methoxybenzoyl)cytidine in 14 ml of THF and 1 ml of methanol was added 8 ml of N-NaOH at 30° C., and the mixture was stirred for 5 minutes. As a result of confirming the state of reaction progress at this time by TLC, the spot for the starting material had disappeared completely and that for the aimed product alone was found, Thereafter, the reaction solution was treated in the same manner as in Example 32, and the obtained residue was recrystallized from methanol to give 0.40 g (52,5%) of 5-deoxy-5-fluoro-$N^4$-(2-methoxybenzoyl)cytidine.

The results of instrumental analysis of the obtained compound were as follows: Melting Point: 196.8°–197.9° C. (Decomposed) $^1$H-NMR (90 MHz, DMSO-$d_6$): 1.34 (d, 3H), 3.93 (s, 3H), 3.5–4.3 (m, 3H), 5.05 (d, 1H), 5.45 (d, 1H), 5.70 (dd, 1H), 7.1–7.8 (m, 4H), 8.15 (d, 1H)

Example 35

To a solution of 447 mg of 5'-deoxy-2',3'-di-0-acetyl-5-fluoro-$N^4$-(3-methylbenzoyl)cytidine in 25 ml of methylene chloride was added 8 ml of 0.5N-NaOH at 14° C., and the mixture was stirred for 5 minutes. As a result of confirming the state of reaction progress at this time by TLC, the spot for the starting material had completely disappeared and that for the aimed product alone was found. Then, 10% hydrochloric acid was added to the reaction solution to adjust the pH to 5, and the resulting solution was extracted with 5 ml of methanol. After extracting the aqueous layer with additional 10 ml of methylene chloride, the organic layers were combined and washed with water (10 ml). After distilling the organic solvent under reduced pressure, the residue was recrystallized from 4 ml of ethanol to obtain 301mg (82.9%) of 5'-deoxy-5-fluoro-$N^4$-(3-methylbenzoyl)cytidine. Melting Point: 146.5°–147.8° C.

Examples 36–44

In accordance with the method of Example 35, the compounds (IV) given in Table 5 were dissolved in a suitable quantity of methylene chloride and then subjected to a selective deacylation in the presence of 0.5N-NaOH as was equivalent to 4 times the mole of each corresponding compound. Therafter, the after-treatments were carded out in the same manner as in Example 35 to obtain the aimed compounds.

Reaction conditions thereof and Yields of the obtained compounds were as given in Table 5, and the physicochemical properties of the compounds were confirmed by instrument analyses such as melting point, NMR etc.

Example 46

52.3 mg of 5'-deoxy-2',3'-di-0-acetyl-5-fluoro-$N^4$-(3,4,5-trimethoxybenzoyl)cytidine was suspended in 0.74 ml of water. After dropwise adding 60 μl of DBU to the suspension with stirring at 26° C., the mixture was stirred at the same temperature for 5 minutes. As a result of confirming the state of reaction progress at this time, the spot for the starting material had completely disappeared and that for the aimed product alone was found. Thereafter, the after-treatment carried out in the same manner as in Example 21 to obtain 5'-deoxy-2',3'-di-0-acetyl-5-fluoro-$N^4$-(3,4,5-trimethoxybenzoyl)cytidine.

The results of instrumental analysis were identical with those of Example 20.

Example 47

52.3 mg of 5'-deoxy-2',3'-di-0-acetyl-5-fluoro-$N^4$-(3,4,5-trimethoxybenzoyl)cytidine trimethoxybenzoyl)cytidine was suspended in 0.74 ml of water. After dropwise adding 55.5 μl of triethylamine to the suspension with stirring at 27° C., the mixture was stirred at the same temperature for 3 hours. As a result of confirming the state of reaction progress at this

TABLE 5

| Example No. | Compound Used In Formula (IV) | | Time (min.) | Reaction Temperature (°C.) | Yield (%) | Melting Point (°C.) (Solvent for Recrystallization) |
|---|---|---|---|---|---|---|
| | $R_1$ | $R_2$ | | | | |
| Example 36 | Me | 4-Nitrophenyl- (1 mmol) | 5 | 12 | 69.8 | 176.5~177.5 (MeOH) |
| Example 37 | Me | 3-Pyridyl- (1 mmol) | 5 | 16 | 60.1 | 164.4~165.0 (MeOH) |
| Example 38 | Me | 2-Furyl- (1 mmol) | 5 | 13 | 59.3 | 177.0~179.0 (EtOH) |
| Example 39 | Me | 2-Thienyl- (1 mmol) | 5 | 15 | 75.1 | 175.5~178.3 (EtOH) |
| Example 40 | Me | Methyl- (1 mmol) | 10 | 0 | 66.0 | 157.5~160.5 (EtOH) |
| Example 41 | Me | 1-Propenyl- (1 mmol) | 15 | 0 | 95.8 | 185.8~187.0 (Isopropyl alcohol/ isopropyl ether) |
| Example 42 | Me | Cyclohexyl- (1 mmol) | 10 | 0 | 90.7 | Obtained as amorphous powder. |
| Example 43 | Me | Benzyl- (1 mmol) | 10 | 0 | 88.6 | Obtained as amorphous powder. |
| Example 44 | Me | Octyloxy- (1 mmol) | 10 | 0 | 88.6 | 107~109 (Ethyl ether) |

Example 45

52.3 mg of 5'-deoxy-2',3'-di-0-acetyl-5-fluoro-$N^4$-(3,4,5-trimethoxybenzoyl)cytidine was suspended in 0.44 ml of water. After dropwise adding 0.36 ml of 10% tetramethylammoniumhydroxide solution to the suspension with stirring at 26° C., the mixture was stirred at the same temperature for 5 minutes. As a result of confirming the state of reaction progress at this time, the spot for the starting material had completely disappeared and that for the aimed product alone was found. Thereafter the after-treatment was carried out in the same manner as in Example 21 to obtain 5'-deoxy-5-fluoro-$N^4$-(3,4,5-trimethoxybenzoyl)cytidine.

The results of instrumental analysis were identical with those of Example 20.

time, the spot for the starting material had completely disappeared and that for the aimed product alone was found. Thereafter, the after-treatment was carried out in the same manner as in Example 21 to obtain 5'-deoxy-5-fluoro-$N^4$-(3,4,5-trimethoxybenzoyl)cytidine.

The results of instrumental analysis were identical with those of Example 20.

Example 48

25.8 g of 5-fluorocytosine was suspended in 100 ml of toluene and 21 g of hexamethyldisilazane, and the suspension was heated to react at 110° C. for 3 hours. After concentration the reaction mixture under reduced pressure, 330 ml of methylene chloride and then 59.3 g of 5-deoxy-1,2,3-tri-0-acetyl-β-D-ribofuranoside were added to the residue. To the ice-cooled solution was added dropwise 62.5 g of anhydrous stannic chloride over a period of in 10 minutes. After the mixture was stirred at room temperature for further 2 hours, 101 g of sodium bicarbonate was added thereto at room temperature, followed by dropwise addition of 35 ml of water over a period of 20 minutes. The mixture was stirred at room temperature for 3 hours, and then the insoluble matters were filtered off. The filtrate was washed with 100 ml of 4% aqueous sodium bicarbonate solution and dried ($Na_2SO_4$). Then, 23 g of pyridine was added to the above solution, into which 56 g of 3,4,5-trimethoxybenzoyl chloride was added at room temperature. After stirring the mixture at room temperature for overnight, the reaction mixture was partitioned between 250 ml of methylene chloride and 125 ml of water. The organic layer was separated and then washed with 125 ml of 4% aqueous sodium bicarbonate solution.

Into the organic layer obtained above was added dropwise 732 ml of N-NaOH solution with stirring while ice-cooling. After stirring for 30 minutes, 200 ml of methylene chloride and 70 ml of methanol were added to the reaction mixture. After adjusting the resulting solution to pH 6 with conc. hydrochloric acid, the organic layer was separated, washed with 160 ml of water and concentrated under reduced pressure. The residue was crystallized from 370 ml of ethyl acetate, and the crystals were filtered. These crystals were recrystallized from 1,150 ml of ethyl acetate to obtain 56.0 g (63.8%) of 5'-deoxy-5-fluoro-$N^4$-(3,4,5-trimethoxybenzoyl)cytidine as crystals.

The results of instrumental analysis of the obtained compound were identical with those of Example 20.

Example 49

To a suspension of 12.9 g of fluorocytosine in 78 ml of pyridine was added 23.1 g of 3,4,5-trimethoxybenzoyl chloride, and the mixture was reacted at 100° C. for 5 hours. After the completion of reaction, the reaction mixture was poured into 300 ml of water at room temperature with stirring. After stirring the resulting mixture for additional 3 hours, the precipitated crystals were collected by filtration, washed with water and then dried to obtain 29.2 g of 5-fluoro-$N^4$-(3,4,5-trimethoxybenzoyl)cytosine.

The crystals obtained above were suspended in 46 ml of toluene and 9.5 g of hexamethyldisilazane, and the mxiture was heated to react at 110° C. for 3 hours. After evaporation of the reaction mxiture under reduced pressure, 270 ml of methylene chloride and 26.8 g of 5-deoxy-1,2,3-tri-0-acetyl-β-D-ribofuranoside was added to the residue, to which 28.2 g of anhydrous stannic chloride was added dropwise over a period of 5 minutes while ice-cooling. After stirring this solution at room temperature for additional I hour, 45.5 g of sodium bicarbonate was added, followed by further of 16 ml of water over a period of 10 minutes. After stirring the mixture for 3 hours, insoluble matters were filtered off, and the filtrate was washed with 45 ml of 6% sodium carbonate solution. To the organic layer obtained according to the above method, 292 ml of N-NaOH was added dropwise with stirring while ice-cooling. After stirring for 30 minutes at the same temperature, 50 ml of methylene chloride and 30 ml of methanol were added to the mixture. After adjusting the mixture to pH 6 with concentrated hydrochloric acid, the organic layer was separated, washed with water and then concentrated under reduced pressure. The residue was crystallized from 150 ml of ethyl acetate, and the crystals were filtered. The filtered crystals were recrystallized from 480 ml of ethyl acetate to obtain 23.2 g (52.8%) of 5'-deoxy-5-fluoro-$N^4$-(3,4,5-trimethoxybenzoyl)cytidine as crystals.

The results of instrumental results of the obtained compound were identical with those of Example 20.

We claim:

1. The process for producing $N^4$-acyl-5'-deoxy-5-fluorocytidine compounds of the formula:

V wherein $R^2$ is alkyl having 1–22 carbon atoms, cycloalkyl having 3–12 carbon atoms, alkenyl having 2–22 carbon atoms, aralkyl, aryl or alkoxy having 1–9 carbon atoms, which comprises treating a compound of the formula (IV),

IV wherein $R^1$ is lower alkyl having 1–6 carbon atoms, unsubstituted aryl or aryl substituted with a methyl, a nitro group or a halogen and $R^2$ is as above, in a solvent with a base to selectively deacylate the 2' and 3' positions of the carbohydrate moiety to produce said fluorocytidine compounds.

* * * * *